United States Patent
Hesse

(10) Patent No.: US 9,581,529 B2
(45) Date of Patent: Feb. 28, 2017

(54) TEST PIECE, TEST METHOD, WIND TURBINE GENERATOR SYSTEM

(71) Applicant: Wobben Properties GmbH, Aurich (DE)

(72) Inventor: Ingo Hesse, Ihlow (DE)

(73) Assignee: Wobben Properties GmbH, Aurich (DE)

( * ) Notice: Subject to any disclaimer, the term of this patent is extended or adjusted under 35 U.S.C. 154(b) by 0 days.

(21) Appl. No.: 14/321,251

(22) Filed: Jul. 1, 2014

(65) Prior Publication Data

US 2015/0007667 A1   Jan. 8, 2015

(30) Foreign Application Priority Data

Jul. 2, 2013 (DE) .................. 10 2013 212 884

(51) Int. Cl.
*G01N 11/00* (2006.01)
*G01N 3/02* (2006.01)
(Continued)

(52) U.S. Cl.
CPC ........ *G01N 3/02* (2013.01); *G01N 3/08* (2013.01); *G01N 3/32* (2013.01); *G01N 33/00* (2013.01);
(Continued)

(58) Field of Classification Search
CPC .... G01N 3/08; G01N 3/32; G01N 2033/0003; G01N 2203/04; G01N 2203/0264; G01N 3/02; G01N 33/00; G01N 2203/0252; B29C 70/20; B29C 70/46; B29C 70/682; B29C 70/36; B29C 70/865; B29C 70/443; B29C 70/48; B64C 9/38; B29B 11/12; B29B 11/16; B29K 2083/005; B29K 2703/00; B29K 2105/24; B29L 2031/308; B29L 2031/3055; B60R 21/00; Y10T 156/15

USPC .......... 73/788; 156/307.3, 536; 296/187.03; 244/213

See application file for complete search history.

(56) References Cited

U.S. PATENT DOCUMENTS 5,869,189 A * 2/1999 Hagood, IV .......... H01L 41/082
310/357
8,100,020 B2 * 1/2012 Kinlen ...................... G01L 1/20
73/760

FOREIGN PATENT DOCUMENTS

DE   10 2006 035 274 A1   2/2008
DE   10 2010 002 131 A1   8/2011
(Continued)

OTHER PUBLICATIONS

Guden et al., "Effect of aluminum closed-cell foam filling on the quasi-static axial crush performance of glass fiber reinforced polyester composite and aluminum/composite hybrid tubes," *Composite Structures* 81:480-490, 2007.

(Continued)

*Primary Examiner* — Lisa Caputo
*Assistant Examiner* — Brandi Hopkins
(74) *Attorney, Agent, or Firm* — Seed Intellectual Property Law Group LLP

(57) ABSTRACT

The invention relates to a test piece for determining a specific material property of a fiber-reinforced plastic composite under applied mechanical loading.

According to the invention, it is provided that an inner core is incorporated in a composite with the fiber-reinforced plastic, the inner core being widened in a transverse axis in relation to the mechanical load in such a way that the composite with the inner core has a greater buckling stability than a comparative body, such as the composite without the inner core, and that the inner core is formed in such a way (Continued)

that an influence on the specific material property to be determined of the fiber-reinforced plastic composite lies in a range of acceptance.

8 Claims, 1 Drawing Sheet

(51) Int. Cl.
*G01N 3/08* (2006.01)
*G01N 3/32* (2006.01)
*G01N 33/00* (2006.01)

(52) U.S. Cl.
CPC .......... *G01N 2033/0003* (2013.01); *G01N 2203/0252* (2013.01); *G01N 2203/0264* (2013.01); *G01N 2203/04* (2013.01)

(56) References Cited

FOREIGN PATENT DOCUMENTS

| | | |
|---|---|---|
| DE | 10 2010 026 620 A1 | 1/2012 |
| DE | 20 2012 008 324 U1 | 11/2012 |
| EP | 0 037 987 A2 | 10/1981 |
| KR | 10-2011-0001645 A | 1/2011 |

OTHER PUBLICATIONS

Palanivelu et al., "Comparison of the crushing performance of hollow and foam-filled small-scale composite tubes with different geometrical shapes for use in sacrificial cladding structures," *Composites: Part B* 41:434-445, 2010.

* cited by examiner

TEST PIECE, TEST METHOD, WIND TURBINE GENERATOR SYSTEM

BACKGROUND

Technical Field

The invention relates to a test piece for determining a specific material property of a fiber-reinforced plastic composite under applied mechanical loading. The invention also relates to a test method and to a use of the test piece for testing a fiber-reinforced plastic composite of a component of a wind turbine generator system, in particular a rotor blade.

Description of the Related Art

Various fiber-reinforced plastic composites are used in technical applications. The fiber-reinforced plastic composites concerned consist of fibers and a corresponding matrix, which provides the necessary bonding of the composite. The profile of properties of these fiber-reinforced plastic composites is determined not only by the selection of fibers and matrix material but also by the orientation of the fibers in the textile fabric. The materials occurring in the composite usually have functional properties that are for a specific purpose within their area of use. Substance-related properties, under some circumstances also geometrical properties, of the individual components are of importance for the properties of the material or composite component obtained. Composite components usually have properties that represent an optimized behavior of the molded part under the effect of a load. The properties may be assigned to a certain strength or a certain stiffness or a certain extensibility with regard to applied mechanical loads.

A pre-requisite for a fiber-reinforced plastic composite component is that, under the effect of a load, the behavior of the composite represents an optimization with respect to the individual components. The development is heading toward optimizing the required properties in combination with the service life in order to withstand cyclical loading over many years.

An example of this is a corresponding fiber-reinforced component of a rotor blade of a wind turbine generator system. Rotor blades are generally made up of appropriate fibers, i.e., primarily glass and/or carbon fibers, in a resin-like LamiMatrix material. These fibers are generally oriented in or along the longitudinal axis of the rotor blade, the exact alignment of the fibers usually being very difficult to control, in dependence on the production process. In the case of rotor blades of wind turbine generator systems, primarily great load effects are exerted. Under these loads, the rotor blades should withstand both the static loading and the very frequent dynamic loading.

Materials testing generally replicates individual stress scenarios on standardized test pieces. On account of the great directional dependence of the properties, the various types of stressing are carried out with different specimens or test pieces longitudinally and transversely in relation to the main direction of the fibers. Apart from the international standardization, tests are described in various national or regional standards, as well as in company-own codes of practice. This produces a broad purview, describing around 20 generic test methods.

The testing on components, parts of structures and complete structures is generally based to a great extent on the stresses or loads that occur in later operation. Strengths, energy absorption, material fatigue and lifetime expectancy are at the forefront. On account of the directional sensitivity and shear sensitivity of the fiber composites, testing forces should as far as possible be applied in the direction intended. The axial error is referred to as misalignment and is subject to narrow limits. Special measuring devices are based on the form and size of the test piece and offer additional supporting and holding devices to avoid classic failure due to misalignment or Euler's buckling. The alignment is performed here by means of mechanical adjusting devices. The force introduction into the test piece should take place over a large surface area, which is achieved by means of force introduction elements. Specimen holders, which operate on the wedge or wedge-screw principle, are usual for this. The exact alignment can be controlled in a simple case with the aid of a strain gage. This is correspondingly applied to the test piece and verified by the measured strain of the specimen.

The measurement or determination of specific material properties with regard to the mechanics for rotor blades or rotor blades in wind turbine generator systems presupposes a high load effect. For the determination of the necessary material properties, the corresponding forces should act on the test piece. The devices for the determination are usually provided with additional buckling support, in order to prevent device- and test-method-specific failure of the component. The often occurring buckling means that there is an abrupt or violent failure of the test pieces and, in principle, does not provide the structure-specific result for the respective fiber-reinforced plastic composite. The attached buckling supports or holding devices have the effect that the axial alignment is ensured and buckling prevented, since corresponding compressive forces act against the bending moment that leads to buckling.

The German Patent and Trademark Office has searched the following prior art in the priority application: DE 10 2006 035 274 A1, DE 10 2010 002 131 A1 and DE 20 2012 008 324 U1.

BRIEF SUMMARY

The present invention provides an alternative to the previous test method setup, since the result may be falsified by the application of the buckling supports. Some embodiments of the invention are directed to an apparatus, a method and a use, in particular a test piece and a corresponding test method and also a use of the test piece, that offers a simplified possible way of measuring mechanical loads or specific material properties in the range of acceptance, in particular with a small measuring error, and to allow higher forces or higher loads than have previously been customary. In particular, the test piece is intended to give the component the necessary stability to reproduce or replicate actual load effects and loading states. In addition, the test piece is intended to allow a comparatively simplified test method that reflects the static and dynamic loads of a rotor blade of a wind turbine generator system without the typical test-induced failure.

An embodiment is based on a test piece for determining a specific material property of a fiber-reinforced plastic composite under applied mechanical loading.

According to one embodiment of the invention, it is provided that an inner core is incorporated in a composite with the fiber-reinforced plastic, the inner core being widened in a transverse axis in relation to the mechanical load in such a way that the composite with the inner core has a greater buckling stability than a comparative body, such as the composite without the inner core, and that the inner core is formed in such a way that an influence on the specific material variable to be determined of the fiber-reinforced plastic composite lies in a range of acceptance. A comparative body, such as the composite without the inner core, has in particular an identical amount of fibers, in particular with the orientation of the amount of fibers of the composite and/or an identical proportion by volume of a fiber-reinforced plastic composite.

One or more embodiments of the invention are directed to a test method and a use of a test piece for testing a fiber-reinforced plastic composite of a component of a wind turbine generator system.

A test piece such as that used in the prior art has proven successful in principle, but has system-inherent weaknesses. The present test piece is more compact and nevertheless set up geometrically more specifically and can stabilize itself against test-falsifying influences. According to an embodiment of the invention, it is provided that the inner core is widened in a transverse axis in relation to the mechanical load in such a way that the composite with the inner core has a greater buckling stability than a comparative body, such as the composite without the inner core; in particular, the comparative body, such as the composite without the inner core, has an identical amount of fibers and/or proportion by volume of the fiber-reinforced plastic composite as the composite with the inner core. The cross section proves to be particularly advantageous here, since it is widened by the inner core and a greater buckling stability is achieved. Under great bending moments or high load effects, the greater cross section prevents mechanical failure due to abrupt bending to evade the loads to be introduced. Security against buckling had to be provided in the prior art by attaching outer guides. In the present case, buckling security is provided by the geometrical parameters of the loaded component itself. The buckling force is based on an axial area moment of inertia of the cross section, in order to achieve greater buckling resistance. It is dependent on the type of stress and the length of the respective test piece and also the cross-sectional form of the test piece. According to an embodiment of the invention, it is additionally provided that this inner core that widens the cross section of the test piece is formed in such a way that an influence on the specific material property to be determined of the fiber-reinforced plastic composite lies in a range of acceptance, in particular a measuring error range. This feature takes up the idea that an additional core can change the composite component as a whole with regard to the material property to be measured. It is taken into account here that there are materials that have little influence or no measurable influence on a composite. This is utilized by incorporating an inner core that has such little influence on the specific material property to be determined that the material property attributable to it lies below the range of error.

One or more embodiments of the present invention allows the application of great loads, representing the actual loading for example of a wind turbine generator system, without means external to the test setup having to be used to achieve a result of an appropriate level. One embodiment of the invention provides a possible way of producing a composite that compensates for the errors of the test method by way of a greater cross section, which prevents buckling under loads. Materials that do not influence the material properties to be measured or lie within the range of acceptance, in particular the measuring error range, are used. This method allows a measurement which on the one hand has a lower range of errors and few failures and on the other hand makes the measuring of fiber-reinforced plastic composites significantly easier. The inner core as an inner stabilization merely achieves greater buckling resistance, but unlike in the prior art does not represent an encasing, or stabilization, that can have a biaxially stronger influence on the measurement of a property of the material composite. In addition, cracks or the propagation of cracks under dynamic loading and the occurrence of material fatigue can be traced more easily, and crack propagation is not slowed down by outer supporting devices and the force dissipation they provide.

It has proven to be particularly advantageous that the inner core restricts the sensitive bending behavior of fiber-reinforced plastic composites and that the measured tensile and compressive strengths correspond to the axial alignments of the fiber composite and can optimize the testing procedure correspondingly. The introduction of force in the test piece can thus take place by way of the axial alignment, without requiring the previously demanded high axial alignment. The test piece thereby allows a usable testing procedure that can reflect the failure of the component without having the faults to be expected of a test method such as buckling.

Further advantageous developments can be taken from the subclaims and provide in detail advantageous possible ways of realizing the explained concept in the course of achieving the object and with regard to further advantages.

In a preferred development, an inner core of the test piece that forms an inner layer of a layer system is provided. In this way, this development offers incorporation of the inner core in a fibrous material that is formed in the manner of a mat or braiding, so that the core can be inserted into this mat-like formation without appreciably changing the geometrical dimensions and the fiber-directed specific properties. This development allows measuring with clear observation of the failure of the respective fiber-reinforced plastic composites along the fibers, since this advantageous layer system can represent clearly the crack fatigue within the fiber-reinforced plastic composites in cross section. In addition, this development is the pragmatic and simplified method for producing a test body. The fiber composite materials formed like mats can thereby retain the geometrical dimensions, and are only thickened in relation to a transverse axis, without changing their own geometrical profiles. Consequently, in the case of this development it can be observed particularly advantageously whether the material properties change in the various axes, and increases in stress can be observed.

In a preferred development, a test piece where the inner core comprises an expanded plastic is provided. This development allows the incorporation of an inner core which, on the basis of the nature of its material and its production process, foaming, is designed in such a way that the influence will lie in the range of acceptance, in particular the measuring error range, of the test method. In order to increase the buckling resistance and/or the loads, this expanded plastic may in particular comprise a filler material that additionally supports the inner core but does not change the material property to be measured of the fiber-reinforced plastic composite. This applies in particular to a test piece with an inner core where the inner core comprises an expanded plastic with filler material. This buckling resistance of the additional fillers is provided exclusively for the benefit of the inner core. The additional filler material also allows an identical buckling resistance with a smaller cross section in comparison with an expanded plastic. It is advantageous to select the respective material that is used for the inner core in dependence on the process. It must always be taken into account that the material properties of the inner core should be so small that they should lie in the range of acceptance, in particular the measuring error range, of the test method. Otherwise, the problem would arise that an integral summation of the material properties with respect to the test piece would not represent the actual specific material properties of a fiber-reinforced plastic composite.

In a preferred development, a test piece that can be described by a substantially rectangular, elongate geometry of the specimen and has outer dimensions of at least 0.5 cm in thickness, at least 2 cm in width and at least 20 cm in length is provided. This development is due to the mechanical load tests or mechanical test methods, which usually use elongate specimens. Tensile and compressive test methods have been used here in particular to describe the geometry of the specimen. The respective test method and the test apparatus for it dictate the geometry of the specimen, especially its width and thickness. In dependence on the length, either the bending moment or the zone of constriction can be obtained. To be able to introduce realistic forces, a certain minimum thickness and width that allow realistic loads, according to the area of use, to be represented should be ensured. For the fiber-reinforced plastic composites, the specimen geometry and specimen structure are important here to reflect the actual loading zones of the respective application areas. The width is responsible for the load distribution of the fixing device and is variable in dependence on the test method and its applied forces and respective test conditions.

In a preferred development, a test piece where the geometry of the specimen has ends tapering to a surface area and adapted to correspond to a fixing device is provided. This development takes account on the one hand of the respective test method and its fixing device, on the other hand of the functional widening of the cross section by way of an inner core with regard to a specific bending moment; other ends may also be provided in principle, for example also widening or other such cross sections such as round, oval or angular cross sections. The cross section should be widened in the region where the highest load effects occur. As recognized by the development, the inner core is usually not required at the ends but at the zones of the highest load effect. These preferably occur in the middle of the specimen if the load effect takes place symmetrically at both ends. Consequently, on account of this development, existing test setups can be used, and no additional outer fastenings or securing rings are needed. The inner core that introduces material properties lying in the range of acceptance, in particular the measuring error range, advantageously does not bring with it any additional modification of the test method or the test apparatus. This development thus leads to a simplification of the test methods previously used.

In a preferred development, it is provided that a fiber-reinforced plastic composite has at least one strain gage. This development reflects existing test methods. However, here there is no observation of the axial alignment to safeguard the test method. Instead, strain gages are used to observe changes of the fibers that on the one hand represent the distribution of the force applied, but on the other hand also allow the material fatigue to be observed. These strain gages can thus be applied to the test piece for dynamic and static load effects, to observe the respective test setup with regard to its axial performance.

In a preferred development, a test piece where the mechanical loads correspond to a tensile loading and/or compressive loading is provided. This development takes up the test methods for fiber-reinforced plastics with regard to their area of use and applies, as the mechanical load, tensile or compressive loading that subjects this test piece to corresponding loading through its fiber-reinforced plastic composite with additionally stabilizing inner core. A test piece with an unchanging characteristic geometry is necessary here in order to be able to represent the respective loading limit in the case of the same test conditions and different materials and to be able to represent differences under the same loading in the case of the same fiber-reinforced plastic composites but different cross sections or different fiber orientations. The test piece also allows increased stability with respect to the previous narrowing of the cross section or buckling under tensile or compressive loads. The filler will not falsify the result here, since it lies in the respective range of acceptance, in particular measuring error range, of the respective test conditions.

In a preferred development, a test piece where the mechanical loads correspond to dynamic loading is provided. This development is due to the fact that, in reality, components with fiber-reinforced plastic composites are usually subjected to dynamic forces. These dynamic forces have a significant influence on the lifetime of a component and its durability. The present test piece allows dynamic loads to be applied without measuring errors or premature failures that have an adverse influence on the assessment of the fiber-reinforced plastic composite being represented by buckling failure.

In a preferred development, a test method using a test piece is provided. This development has the effect that the test piece can be used in such a way that the previously known test methods can be used and adapted to the application areas. In this way, both higher dynamic loads and higher static loads are possible, since the probability of failure is reduced by the additional inner core and the test result has a smaller measuring error range. The test method can be specifically adapted by the respective test piece and its geometry and utilizes the advantages of the test piece with a corresponding inner core. In this case, the specific material properties determined reflect the respective fiber-reinforced plastic composites without being falsified by an additional element such as the inner core.

In a preferred development, the test piece is used for testing a fiber-reinforced plastic composite of a component of a wind turbine generator system, in particular a rotor blade. This development relates to the fact that especially static and dynamic loads on wind turbine generator systems occur in particular on the rotor blades. Consequently, special test methods or exact test methods should be used here in order to be able to reflect the respective static and dynamic loads and be able to represent material properties. The test piece offers the opportunity not only of material selection but also of modifying the test method with regard to higher forces, which could allow further development of rotor blades. The forces acting, which are at present restricted by technical aspects of the test, can now be changed over to actual values, since the probability of failure caused by the excessively narrow cross section has been reduced. The test piece produces accurate and realistic values of the respective fiber-reinforced plastic composite for a test method for a respective rotor blade.

BRIEF DESCRIPTION OF THE SEVERAL VIEWS OF THE DRAWINGS

Exemplary embodiments of the invention are described below on the basis of the drawing in comparison with the prior art, which is partly likewise presented. The drawing is not necessarily intended to show the exemplary embodiments to scale, but rather takes a schematized and/or slightly distorted form wherever this is useful for explanatory purposes. For additions to the teachings that are directly evident from the drawing, reference is made to the relevant prior art. At the same time, it must be taken into account that a wide variety of modifications and changes relating to the form and detail of an embodiment can be made without departing from the general concept of the invention. The features of the invention that are disclosed in the description, in the drawing and in the claims may be essential to the development of the invention both individually and in any desired combination. Moreover, the scope of the invention covers all combinations of at least two of the features disclosed in the description, the drawing and/or the claims. The general concept of the invention is not limited to the exact form or the detail of the preferred embodiment shown and described below or limited to a subject matter that would be restricted in comparison with the subject matter defined in the claims. Where dimensional ranges are specified, values lying within the stated limits are also intended to be disclosed as limit values and able to be used and claimed as desired.

Further advantages, features and details of the invention emerge from the following description of the preferred exemplary embodiments and on the basis of the drawings, in which specifically.

DETAILED DESCRIPTION

Figure 1:
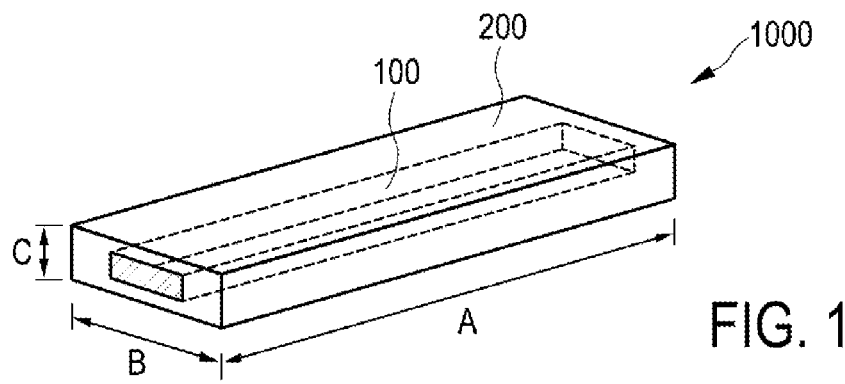
FIG. 1 shows a schematized representation of the form of the specimen.

In FIG. 1, the outer geometrical dimensions of the test piece 1000 with an inner core 100 and an outer fiber-reinforced plastic composite 200 are represented by letters A-C, creating the characteristic impression of a right-angled elongate specimen. The length A, which should be at least 20 cm, is in principle advantageously much greater than the width, characterized by the letter B. In height, characterized by the letter C, the test piece is at least 0.5 cm thick. The specimen presented here represents the fiber-reinforced plastic composite in the form of a test piece 1000, which is used in order to be able to reflect mechanical loads, such as for example tension or compression. The specific material properties determined can be represented by the characteristic geometry of the specimen. In this case, the influence of the geometry of the specimen on the respective result is dependent on the test conditions. The present test piece 1000 shows the typically represented fiber-reinforced plastic composite 200, which has a certain length in an axial alignment, but usually has smaller heights in the other axes.

Figure 2:
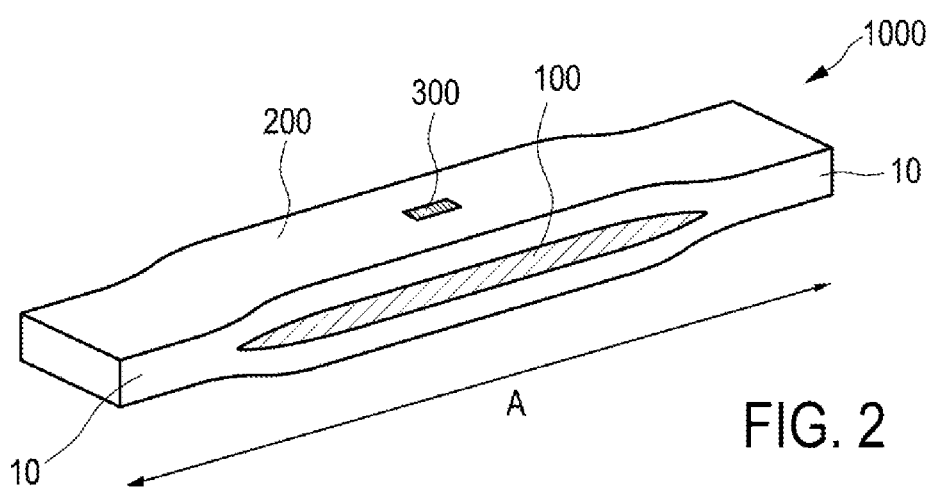
FIG. 2 shows a schematized representation of the test piece in a preferred exemplary embodiment.

In FIG. 2, a test piece 1000 is schematically represented, the characteristic geometry of the specimen here having been modified wherein the inner core 100 is presented with respect to the fiber-reinforced plastic composite 200 in the longitudinal axis A. Here, the fiber-reinforced plastic composite takes the form of a layer system that includes the inner core as an inner layer. The respective ends 10 taper and, for the clamping device, correspondingly only comprise the fiber-reinforced plastic. The inner core 100 incorporated here is an additional material that widens the cross section for respective loading measurements without falsifying the test result. The cross section serves the purpose of achieving a certain resistance along, as far as possible parallel to, the fiber orientation (axis A). The variable to be measured, the material properties in the axial alignment of the fiber-reinforced plastic composite, is not influenced by this core, but is stabilized against buckling. The strain gage 300 applied to the surface of the test piece 1000 can measure the change in the units of length due to applied loads.

Figure 3:
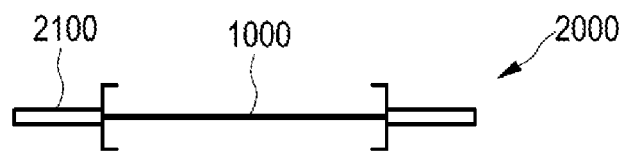
FIG. 3 shows a schematized representation of a clamping device for a test method in a preferred exemplary embodiment.

In FIG. 3, a test apparatus 2000 is stylized in the form of an engaging fixing device, which engages uniaxially from both sides. The test piece 1000 is clamped here at both ends in the fixing device of the test stand 2100 and undergoes directed loading that is distributed in the component, so that the inner core can counteract failures such as buckling or narrowing of the cross section. In a way corresponding to the test method, the applied forces here may be static loads such as tensile or compressive stresses or dynamic loads. The test setups for fiber-reinforced plastic composites that are used in a wind turbine generator system, in particular in a rotor blade, are preferably stylized by the test apparatus.

LIST OF DESIGNATIONS 10 ends of the test piece
100 inner core
200 fiber-reinforced plastic composite
300 strain gage
1000 test piece
2000 test apparatus
2100 fixing device

The invention claimed is:

1. A test piece including a specimen of fiber-reinforced plastic composite for determining a specific material property of the fiber-reinforced plastic composite under applied mechanical loading, the test piece comprising:
   an inner core incorporated in the composite with the fiber-reinforced plastic composite, the inner core being widened in a transverse axis in relation to the applied mechanical load, wherein the fiber-reinforced plastic composite with the inner core has a greater buckling stability than the fiber-reinforced plastic composite without the inner core, and wherein the inner core's influence on the specific material property to be determined of the fiber-reinforced plastic composite lies in a range of measuring error,
   wherein the test piece includes an outer surface and at least one strain gage located on the outer surface, wherein mechanical loads are applied to the test piece corresponding to at least one of tensile loading and compressive loading, wherein the mechanical loads correspond to dynamic loading, and
   the test piece including ends tapering to a surface area and adapted to fit into a fixing device.

2. The test piece as claimed in claim 1, wherein the inner core forms an inner layer of a layer system.

3. The test piece as claimed in claim 1, wherein the inner core comprises an expanded plastic that includes a filler material.

4. The test piece as claimed in claim 1, wherein the test piece can be described by a substantially rectangular, elongate geometry and has outer dimensions of at least 0.5 cm in thickness, at least 2 cm in width and at least 20 cm in length.

5. The test piece as claimed in claim 1 wherein the fiber-reinforced plastic composite is a layer system that includes the inner core as an inner layer and the tapered ends do not include the inner core.

6. A method of testing a test piece as claimed in claim 1, the method comprising:
   clamping a first end of the test piece in a first fixing device of a test stand;

clamping a second end of the test piece in a second fixing device of the test stand; and applying at least one of a tensile load and a compressive load to the test piece.

7. A method of manufacturing a component of a wind turbine generator system, the method comprising:

testing the test piece as claimed in claim 1; and using the test piece to form the component.

8. The method as claimed in claim 7, wherein the component of the wind turbine generator system is a rotor blade.

* * * * *